(12) United States Patent
Senatorov

(10) Patent No.: US 6,703,242 B1
(45) Date of Patent: Mar. 9, 2004

(54) DARK-FIELD MICROSCOPY VISUALIZATION OF UNSTAINED AXONAL PATHWAYS USING OIL OF WINTERGREEN

(75) Inventor: Vladimir Senatorov, Rockville, MD (US)

(73) Assignee: Vladimir V. Senatorov, Rockville, MD (US)

( * ) Notice: Subject to any disclaimer, the term of this patent is extended or adjusted under 35 U.S.C. 154(b) by 0 days.

(21) Appl. No.: 10/334,313

(22) Filed: Dec. 31, 2002

Related U.S. Application Data

(60) Provisional application No. 60/343,900, filed on Jan. 2, 2002.

(51) Int. Cl.⁷ .............................................. G01N 33/48

(52) U.S. Cl. ..................... 436/63; 436/164; 435/40.5; 435/40.52

(58) Field of Search .................. 436/63, 164, 171; 435/40.5, 40.52

(56) References Cited

U.S. PATENT DOCUMENTS

| 6,042,874 A | 3/2000 | Visinoni et al. |
| 6,465,208 B1 | 10/2002 | Rogers |
| 6,472,216 B1 | 10/2002 | Chiang |

OTHER PUBLICATIONS

Price PG, Fisher AW. Location of single neurons containing HRP for electron microscopy. Brain Res. Bull., 1977, 2: 495–497.

Grace AA, Llinas R. Morpholigical artifacts induced in intracellulary stained neurons by dehydration: Circumvention using rapid dimethyl sulfoxide clearing. Neuroscience, 1985; 16:461–475.

Becker DL, Dekkers J, Navarrete R, Green CR, Cook JE. Enhancing the laser scanning confocal microscopic visualization of Lucifer yellow filled cells in whole–mounted tissue. Scanning Microsc., 1991; 5: 619–624.

Martin P, Ohno M, Southerland SB, Mailman RB, Suzuki K. Heterotypic sprouting of serotonergic forebrain fibers in the brindled mottled mutant mouse. Brain Res. Dev. Brain Res., 1994; 77: 215–225.

Hermes ML, Coderre EM, Buijs RM, Renaud LP. GABA and glutamate mediate rapid neurotransmission from suprachiasmatic nucleus to hypothalamic paraventricular nucleus in rat. J. Physiol. (Lond), 1996; 496: 749–757.

Senatorov VV. Dark–field microscopy visualization of unstained axonal pathways using oil of wintergreen. J. Neurosci. Meth., 2002, 113, 59–62.

*Primary Examiner*—Maureen M. Wallenhorst

(57) ABSTRACT

The present invention provides the visualization of the fiber architecture in the nervous tissue without staining. The major principle of the method is to make the neural tissue transparent in normal light, and to utilize the ability of neuronal fibers to deflect and deviate light directed from the side to render them visible. The method involves the preparation of thick sections (more than 200 mm) of the nervous tissue, their fixation in paraformaldehyde and dehydration in ethanol. Oil of wintergreen (methyl salicylate) is utilized to make the tissue transparent under normal (bright-field) light. Dark-field illumination is used to create illuminating rays of light arriving at an angle exceeding the collecting angle of the objective lens, thus causing only the axonal pathways to be visible as a bright silver silhouette against a dark background.

1 Claim, 1 Drawing Sheet

DARK-FIELD MICROSCOPY VISUALIZATION OF UNSTAINED AXONAL PATHWAYS USING OIL OF WINTERGREEN

RELATED APPLICATION

This application for a patent claims the benefits of the earlier filed provisional application 60/343,900 with filing date Jan. 2, 2002.

FEDERALLY SPONSORED RESEARCH OR DEVELOPMENT

Not Applicable

SEQUENCE LISTING, A TABLE, OR COMPUTER PROGRAM LISTING COMPACT DISK APPENDIX

Not Applicable

BACKGROUND OF THE INVENTION

The invention relates to a method of visualizing morphological structure in the nervous tissue. Despite enormous progress in the development of new techniques for studying central nerve pathways, few methods are available for visualization of the whole fiber architecture in the neural tissue. The most known methods for myelin sheath staining are iron-haematoxylin (Weil, 1928; Anderson, 1929), Luxol fast blue (Kluver and Barrera, 1953), Sudan-black (Olson and Traub, 1990), and a labeling with Black-gold (Schmued and Slikker, 1999). Another popular technique is axonal silver staining (Bodian; 1937, Davenport, 1929; Glees, 1946; Nauta, 1950; Beltramrino et al., 1993). In the last decades, methodological research primarily focused on tracing: single axonal pathways with markers moving by axonal transport (Kristensson and Olsson, 1971; Gerfen and Sawchenko, 1984; Katz et al, 1984; Schmued and Fallon, 1986; et al.) or with lipid soluble dyes drifting within the cell membrane (Honig and Hume, 1986).

While these and other techniques proved to be beneficial, they have certain limitations. Firstly, most known methods involve some kind of staining or dye incorporation. Secondly, they are rather sophisticated, labor intensive and time consuming. In addition, many of them require expensive reagents. Finally, the absolute majority of known tract tracing techniques deal with relatively thin (less than 60 $\mu$m) sections of neural tissue. A major drawback of thin sections is that they are virtually two-dimensional, and many sections should be pooled together for three-dimensional reconstruction of large segments of the fiber system in the CNS. Several studies dealing with 400–500 $\mu$m brain slices are focused on the morphology of single neurons pre-filled by intracellular injection of dye (Grace and Llinas, 1985; Hermes et al., 1996).

SUMMARY OF THE INVENTION

The purpose of this invention is to provide an extremely simple morphological technique for visualization of axonal pathways in thick sections of the nervous tissue.

To overcome the limitations of many previously developed methods, I chose an approach that utilizes thick (more than 200 $\mu$m) sections of the nervous tissue but does not involve staining. After years of experimentation, I have developed a technique, by which the whole fiber architecture of a thick slice of nervous tissue is made visible without using any dyes or other foreign substances.

This invention is based on a discovery that axonal bundles can be made visible without any staining, solely using their ability to deflect and deviate light rays directed at an angle exceeding the collecting angle of the objective lens (Senatorov 2002a and 2002b). The main principle of the invention is to make neural tissue transparent under normal (bright-filed) light, and then use the ability of axonal pathways to scatter light for observation using dark-field illumination.

One of the most attractive features of this invention is that even the three-dimensional structure of the whole white matter in the nervous tissue slice can become clearly visible (FIG. 1A). Due to its extreme simplicity, the invention can be applied using basic microscopic equipment and a minimal set of reagents. As the present invention does not involve any kind of staining or dye incorporation, it does not require any expensive reagents and it consumes only a minimal amount of labor and time.

DESCRIPTION OF THE PHOTOGRAPHS

As the invention is not capable of being illustrated in an ink drawing, it will be further illustrated in the following photographs by way of examples, wherein FIG. 1A is a photomicrograph showing fiber tract visualization in the frontal slice of the adult rat brain at the level of the forebrain by the method of the present invention.

Figure 1:
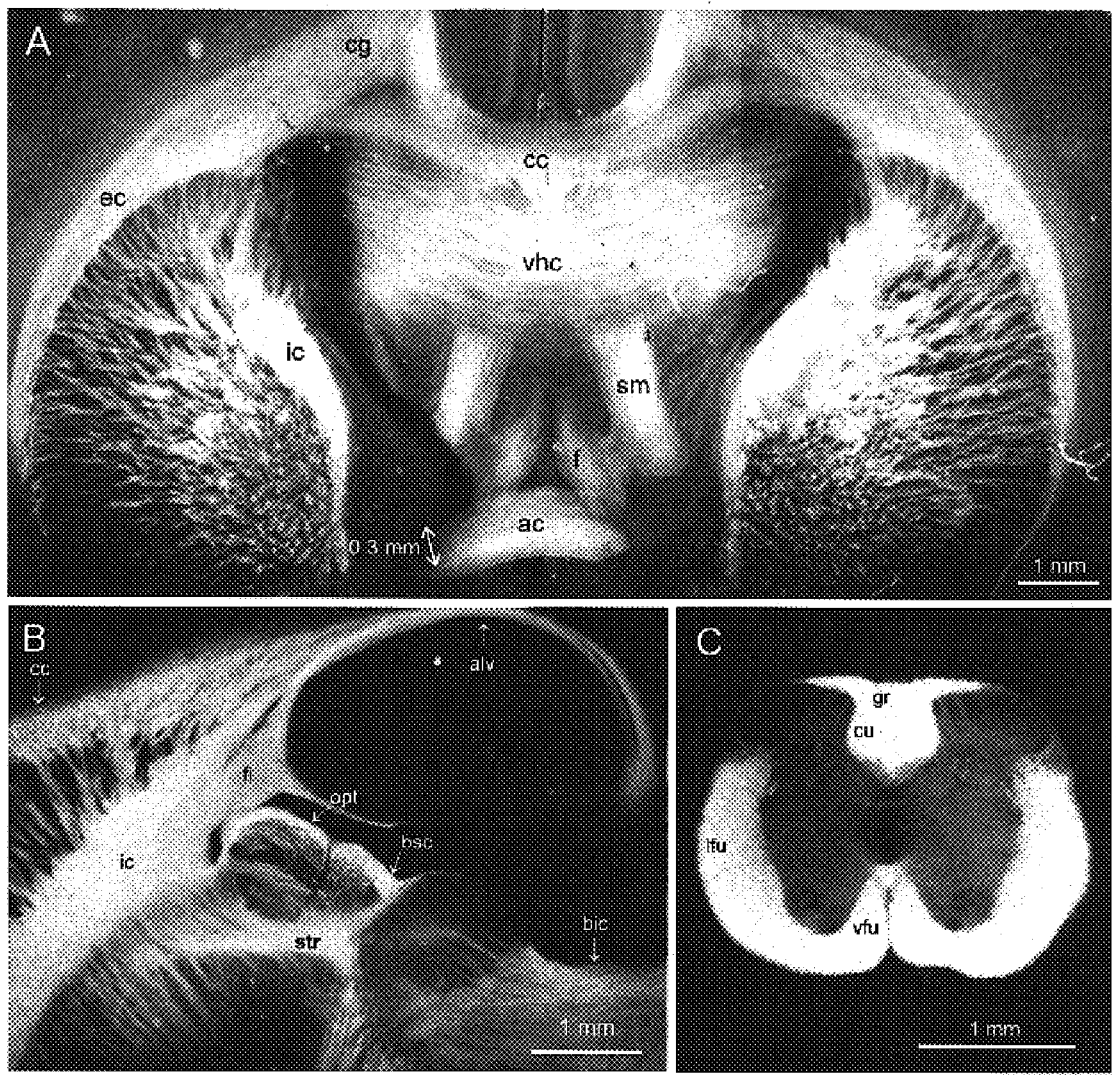
FIG. 1B is a photomicrograph showing the visualization of fiber in the horizontal slice of the adult rat brain at the forebrain and thalamus level by the method of the present invention.
FIG. 1C is a photomicrograph showing fiber organization in the spinal cord (thoracal segment) of a 16-day old rat by the method of the present invention.

Abbreviations: ac, anterior commissure; alv, alveus hippocampus; bic, brachium inferior colliculus; bsc, brachium superior colliculus; cc, corpus callosum; cg, cingulum; cu, cuneate fasciculus; ec, external capsule; f, fornix; fi, fimbria; gr, gracile fasciculus; ic, internal capsule; lfu, lateral funiculus; ml, medial lemniscus; opt, optical tract; sm, stria medullaris; str, superior thalamus radiation; vhc, ventral hippocampal commisure; vfu, ventral funiculus

DETAILED DESCRIPTION OF THE INVENTION

Experimental
Material and Methods

The method was originally developed using fixed brains samples of calf (purchased in a local food store), male adult Wistar rats (Institute for Experimental Medicine, Russia) and postmortem human brain samples ($1^{st}$/Medical Institute, St. Petersburg, Russia). Later its usefulness was also verified on adult female and neonatal (16 days) Wistar rats (Charles-River, Canada) and adult C3H/HeJ mice (The Jackson Laboratory, Bar Harbor, Maine). The experiments also employed fixed tissue pre-used in electrophysiological or morphological experiments as described elsewhere (Senatorov et al., 1993, 1995). Briefly, during electrophysiological experiments, 400 or 500 $\mu$m slices were maintained for up to 8 hours at room temperature in oxygenated artificial cerebrospinal fluid, and then fixed by the immersion in 4% paraformaldehyde in 0.1 M phosphate buffer, pH=7.4 (PPB). In morphological experiments, rats or mice were overanaethetized with sodium pentobarbital and perfused transcardially with 200–300 ml of PPB and then brains were postfixed by the immersion in PPB. Calf brains and postmortem human brains were fixed by the immersion in 10% formalin. Following fixation, 200–600 μm or thicker sections were cut with a set of parallel blades. Alternatively, and upon availability, a chopper or any device with a vibrating blade, such as a vibratome or vibrating blade microtome, might be used. After fixation, sections were dehydrated in the ascending series of ethanol—70, 95 and 100%—10 min each, and were left in a second change of 100% alcohol for 1–2 h. Finally, sections were immersed in methyl salicylate (also known as oil of wintergreen) for about 10–20 min, until they became visually transparent. For observation under a microscope, the slices were mounted on glass slides and coverslipped. Fiber architecture was observed using a low-power objective, e.g. 2×, 5×or 10×with a numerical aperture lower than the numerical aperture of the dark-field condenser.

Results

Transparency of the slices was achieved through clearing with methyl salicylate, which together with other organic solvents such as xylene, chloroform and dimethyl sulfoxide, is known for dissolving neuronal lipids and causing neural tissue to become more transparent (Becker et al., 1991; Hermes et al., 1996; Grace and Llinas, 1985). However, for this method, xylene, chloroform and dimethyl sulfoxide do not work. As a result of methyl salicylate exposure, lipids and some other organic molecules are removed from the brain tissue slices, which make them transparent and practically 'invisible' under normal illumination. However, when slices are illuminated by a hollow cone of light striking from the dark-field condenser at an angle exceeding the collecting angle of the objective lens, the axonal bundles become clearly visible in the form of a bright silver-white substance against a dark background (FIG. 1). In the experiments, frontal, sagittal, and horizontal sections of the brain have been successfully used without any difference in results (FIGS. 1A and 1B). In the brain regions containing large axonal bundles running within a surrounding mass of gray matter such as the forebrain, the three-dimensional course of axonal bundles can be clearly visible due to gray matter transparency (FIG. 1A). When neural slices were immersed in methanol without prefixation in paraformaldehyde, the preparation should be viewed; immediately after a very short (few minutes) incubation in methyl salicylate. Otherwise, the portion of thinner fiber bundles quickly become darker and less visible. The brain slices prefixed with paraformaldehyde required longer methyl salicylate immersion and could be kept there for days or even weeks.

The current technique is usable for verification of axonal pathways in slice preparations previously used in electrophysiological experiments, e.g. cortico-striatal and thalamic slices, and brain slices containing embryonic transplants. For example, FIG. 1B shows a photo of a horizontal slice through the rat thalamus. I has used this slice in an electrophysiological experiment to study the thalamo-cortical connection, and found the technique to be very successfully to choose the best angle to cut a 400 μm horizontal brain slice, which contained axons running all the way through the auditory thalamo-cortical pathway.

In addition to brain tissue, spinal cord slices have also been used, and it is found that the technique works equally well (FIG. 1C). Methodologically, the results obtained from either adult or very young rats are not different. The technique works equally well in the brain tissue of mice, calf, and postmortem human brain.

To find the optimal conditions, brain slices of different thickness have been cut and it has been found that a thickness of 300–500 μm is best for the visualization of neural bundles in small animals. 200 μm is a minimal thickness for slices that could be successfully used, as axonal fiber bundles are not visible in thinner slices. On the other hand, thicker slices are more difficult to view in the small animals because of the accumulating volume of white tissue. Considering that in large animal and human brains, large fiber bundles extend beyond the slice thickness of 400–600 μm, it should be noted that there is no immediate limitation on maximal slice thickness in technique per se. Depending on the microscope specifications and anatomical organization of the observed brain region, sometimes thicker slices (1 mm and more) might serve better. Another peculiarity of this method is that fiber architecture can be effectively observed only under low magnification, such as with 2×, 5×or 10× objectives. Choosing the proper distance between the condenser and the specimen to provide appropriate illumination is very important. While I needed some practice for setting up good dark-field illumination, obtaining results is not that difficult. The first successful experiments have been carried out in home laboratory conditions.

PUBLICATIONS

Anderson J. How to stain the nervous system, E. Livingstone: Edinburgh, 1929. Becker D L, Dekkers J, Navarrete R, Green C R, Cook J E. Enhancing the laser scanning confocal microscopic visualization of Lucifer yellow filled cells in whole-mounted tissue. Scanning Microsc., 1991; 5: 619–24.

Beltramino C A, de Olmos J S, Gallyas F, Heimer L, Zaborszky L. Silver staining as a tool for neurotoxic assessment. NIDA Res. Monogr., 1993; 136:101–26; discussion 126–32. Bodian D. The staining of nervous tissue with activated protorzol. The role of fixatives. Anat. Res., 1937; 69: 153–62.

Davenport H A. Silver impregnation of nerve fibers in celloidin sections. Anat. Rec., 1929; 44: 79–83.

Gerfen C R, Sawchenko P E. An anterograde neuroanatomical tracing method that shows the detailed morphology of neurons, their axons and terminals: immunohistochemical localization of an axonally transported plant lectin, Phaseolus vulgaris leucoagglutinin (PHA-L). Brain Res., 1984; 290: 219–38.

Glees P. Terminal degeneration within the central nervous system as studied by a new silver method. J. Neuropath. Exp. Neurol., 1946; 5: 54–9.

Grace A A, Llinas R. Morphological artifacts induced in intracellularly stained neurons by dehydration: Circumvention using rapid dimethyl sulfoxide clearing. Neuroscience, 1985; 16: 461–75.

Hermes M L, Coderre E M, Buijs R M, Renaud L P GABA and glutamate mediate rapid neurotransmission from suprachiasmatic nucleus to hypothalamic paraventricular nucleus in rat. J. Physiol. (Lond), 1996; 496: 749–57.

Honig M G, Hume R I. Fluorescent carbocyanine dyes allow living neurons of identified origin to be studied in long-term cultures. J. Cell. Biol. 1986; 103, 171–87.

Katz L C, Burkhalter A, Dreyer W J. Fluorescent latex microspheres as a retrograde neuronal marker for in vivo and in vitro studies of visual cortex. Nature, 1984; 310: 498–500.

Kluver H and Baffera E. A method for the combined staining of cells and fibers in the nervous system, J. Neuropath. Exp. Neurol., 1953, 12, 400–403.

Kristensson K, Olsson Y. Retrograde axonal transport of protein. Brain Res., 1971; 29: 363–5.

Nauta W J. über die sogenannte terminale Degenerations im Zentralnervensystem und ihre Darstellung dutch Silbrimpregnation. Arch. Neurol. Psychiatr., 1950; 66: 353–76.

Olson K R, Traub R K. Visual enhancement of myelinated tissues in the central nervous system of the rat using Sudan black B. Stain Technol., 1990, 65, 151–3.

Schmued L C, Fallon J H. Fluoro-Gold: a new fluorescent retrograde axonal tracer with numerous unique properties. Brain Res., 1986; 377: 147–54.

Schmued L, Slikker W Jr. Black-gold: a simple, high-resolution histochemical label for normal and pathological myelin in brain tissue sections. 1999, Brain Res, 837, 289–97.

Senatorov V V. Dark field microscopy visualization of unstained axonal pathways using oil of wintergreen. Provisional patent application No. 60/343,900, 2002a, filing date Jan. 2, 2002.

Senatorov V V Dark field microscopy visualization of unstained axonal pathways using oil of wintergreen. J. Neurosci. Meth., 2002b, 113, 59–62.

Senatorov W V, Nyakas C, Fulop Z. Visualization of the outgrowing axons of grafted neurons by anterograde labeling with *Phaseolus vulgaris* leucoagglutinin in the motor cortex of the rat. Restor. Neurol. Neurosci, 1993; 5: 337–45.

Senatorov V V, Vilagi I, Tarnawa I, Banczerowski-Pelyhe I, Fulop Z. Low extracellular magnesium unmasks N-methyl-D-aspartate-mediated graft-host connections in rat neocortex slice preparation. Neuroscience. 1995: 64: 443–58.

Weil A. A rapid method for staining myelin sheaths. Archives of neurology and psychiatry, 1928; 20: 392–93.

I claim:

1. A method visualizing axonal pathways in nervous tissues, comprising steps of
   a) clearing a fixed and dehydrated unstained nervous tissue with methyl salicylate to make it transparent in normal, bright-field light; and
   b) visualizing axanol pathways in the transparent unstained nervous tissue with objective lens by using a dark-microscopic field illumination to create rays of light arriving at an angle exceeding a collecting angle of the objective lens.

* * * * *